US008551452B2

(12) United States Patent
Wurtman

(10) Patent No.: US 8,551,452 B2
(45) Date of Patent: Oct. 8, 2013

(54) URIDINE DIETARY SUPPLEMENTATION COMPLIANCE METHODS AND USE THEREOF

(75) Inventor: Richard Wurtman, Boston, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 982 days.

(21) Appl. No.: 12/264,055

(22) Filed: Nov. 3, 2008

(65) Prior Publication Data

US 2009/0117051 A1    May 7, 2009

Related U.S. Application Data

(60) Provisional application No. 60/996,146, filed on Nov. 2, 2007.

(51) Int. Cl.
*A61B 5/055* (2006.01)
*A61K 49/00* (2006.01)

(52) U.S. Cl.
USPC ........ 424/9.3; 424/9.341; 424/9.37; 424/9.44

(58) Field of Classification Search
USPC ............... 514/49–51, 274; 424/639, 646, 9.3, 424/9.31, 9.37, 9.44
See application file for complete search history.

(56) References Cited

U.S. PATENT DOCUMENTS

| | | | |
|---|---|---|---|
| 4,221,784 A | 9/1980 | Growdon et al. | |
| 4,960,759 A | 10/1990 | De Luca et al. | |
| 5,141,943 A | 8/1992 | Naguib et al. | |
| 5,190,948 A | 3/1993 | Materazzi et al. | |
| 5,470,838 A | 11/1995 | Von Borstel | |
| 5,567,689 A | 10/1996 | Sommadossi et al. | |
| 5,583,117 A | 12/1996 | Von Borstel | |
| 5,601,829 A | 2/1997 | Quintanilla Almagro et al. | |
| 5,723,449 A | 3/1998 | Sommadossi et al. | |
| 5,962,459 A | 10/1999 | Piazza et al. | |
| 5,977,174 A | 11/1999 | Bradley et al. | |
| 6,103,703 A | 8/2000 | Renshaw et al. | |
| 6,132,724 A | 10/2000 | Blum | |
| 6,191,154 B1 | 2/2001 | Landreth et al. | |
| 6,258,795 B1 | 7/2001 | Von Borstel et al. | |
| 6,274,563 B1 | 8/2001 | Von Borstel et al. | |
| 6,316,426 B1 | 11/2001 | Von Borstel et al. | |
| 6,472,378 B2 | 10/2002 | Von Borstel | |
| 6,989,376 B2 | 1/2006 | Watkins et al. | |
| 7,105,498 B2 | 9/2006 | Von Borstel et al. | |
| 2001/0005719 A1 | 6/2001 | Von Brostel | |
| 2003/0114415 A1 | 6/2003 | Wurtman et al. | |
| 2005/0017716 A1 | 1/2005 | Fiat | |
| 2005/0027004 A1 | 2/2005 | Kyle et al. | |
| 2005/0203053 A1 | 9/2005 | Wurtman et al. | |
| 2006/0069061 A1 | 3/2006 | Wurtman et al. | |
| 2006/0241077 A1 | 10/2006 | Wurtman et al. | |
| 2007/0004670 A1 | 1/2007 | Wurtman et al. | |
| 2009/0105189 A1 | 4/2009 | Wurtman et al. | |
| 2010/0022567 A1 * | 1/2010 | Wurtman et al. ............. 514/274 |

FOREIGN PATENT DOCUMENTS

| | | |
|---|---|---|
| EP | 0 178 267 | 4/1986 |
| EP | 0 348 360 | 12/1989 |
| EP | 0 462 075 | 12/1991 |
| JP | 07/215879 A | 8/1995 |
| JP | 09/30976 A2 | 2/1997 |
| JP | 2001/233776 A2 | 8/2001 |
| WO | WO97/43899 A1 | 11/1987 |
| WO | WO89/03837 A1 | 5/1989 |
| WO | WO 95/05180 | 2/1995 |
| WO | WO 97/45127 | 12/1997 |
| WO | WO 00/06174 A1 | 2/2000 |
| WO | WO00/50043 A1 | 8/2000 |
| WO | WO 02/089787 | 11/2002 |
| WO | WO 2005/086619 | 9/2005 |
| WO | WO 2005/122767 A1 | 12/2005 |

OTHER PUBLICATIONS

S.M. Babb et al., Differential effect of CDP-choline on brain cytosolic choline levels in younger and older subjects as measured by proton magnetic resonance spectroscopy, Psychopharmacology, 127, 88-94, 1996.*
Bruce M. Cohen et al., Decreased Brain Choline Uptake in Older Adults- An in viov Proton Magnetic Resonance Spectroscopy Study, JASMA, 274, 902-097, 1995.*
Mehmet Cansev et al., Oral uridine-5'monophosphate (UMP) increases brain, CDP-choline levels in gerbils, Brain Research, 1058, 101-108, 2005.*
Pravat K. MandalMagnetic Resonance Spectroscopy (MRS) and its application in Alzheimer's Disease, Concepts in Magnetic Resonance Part A , vol. 30A(1), 40-64, 2007.*
Peter H Silverston et al., Annals of Genreral Hospital Psyhciatry, (2004, 3:13, 1-7).*
Ingraham et al., "Nucleoside Diphosphokinase from *Salmonella typhimurium*," Chapter 48 in Methods in Enzymology, LI(vol. 51), Hoffee et al. (eds.), New York, NY, 1978, Academic Press, only pp. 371 and 375 supplied; assorted portions of other chapters were also supplied including pp. 305, 306, 318, 327, 329 and 330.
De Bruin et al, "Effects of Uridine/Choline on cognitive deficits in spontaneously hypertensive rats" Program No. 184.16. 2002 Abstract Viewer/Itinerary Planner. Washington, DC: Society for Neuroscience, 2002. Online: http://sfn.scholarone.com/itin2002/index.html.
Wurtman et al, Effect of oral CDP-choline on plasma choline and uridine levels in humans. Biochem Pharmacol. Oct. 1, 2000;60(7):989-92.

(Continued)

*Primary Examiner* — Michael G Hartley
*Assistant Examiner* — Jagadishwar Samala
(74) *Attorney, Agent, or Firm* — Pearl Cohen Zedek Latzer, LLP

(57) ABSTRACT

This invention relates to determining the compliance of a subject receiving dietary supplementation with uridine or a uridine source. Specifically, the invention relates to the use of MRS for measuring an increase in brain compounds resulting from dietary supplementation with uridine or a uridine source.

14 Claims, No Drawings

(56) References Cited

OTHER PUBLICATIONS

Petersen et al, Mild cognitive impairment: clinical characterization and outcome. Arch Neurol. Mar. 1999;56(3):303-8. Erratum in: Arch Neurol Jun. 1999;56(6):760.
Agnati et al, Intravenous uridine treatment antagonizes hypoglycaemia-induced reduction in brain somatostatin-like immunoreactivity. Acta Physiol Scand., Apr. 1986;126(4):525-31.
Zaffaroni, et al (1951) "Adrenal Conversion of C14 Labeled Cholesterol and Acetate to Adrenal Cortical Hormones" Journal of the American Chemical Society, 73, 1390-1391.
Marcus, et al (1990) "Water soluble vitamins" Ch. 63 in Goodman & Gilman's The Pharmacological Basis of Therapeutics 1530 and 1542-1544.
Sitaram, et al (1978) "Human Serial Learning: Enhancement with Arecholine and Choline and Impairment with Scopolanrine" Science 201, 274-276.
Hock, et al (2000) "Increased CSF Levels of Nerve Growth Factor in Patients with Alzheimer's Disease" Neurology 54 2009-2011.
Savendahl, et al (1997) "Prolonged Fasting in Humans Results in Diminished Plasma Choline Concentrations But Does Not Cause Liver Dysfunction" American Journal of Clinical Nutrition, 66, 622-625.
A Lehninger, Biochemistry, Second edition Worth Publishers, Inc, New York NY Jul. 1978, pp. 735-737 supplied.
Beers, et al (1999) "Merck Manual of Diagnosis and Therapy" 977, 1025, 1027, 1038, 1471, 1472, 1475 and 2417.
Weiss (1995) "Metabolism and Action of CDP-Chlorine As an Endogenous Compound and Administered Exogenously As Citicoline." Life Science vol. 56 No. 9 637-660.
Alvarez, et al (1997) "Citicoline Improves Memory Performance in Elderly Subjects." Methods Find Exp Clin. Pharmacol. 201-210.
Petkov, et al (1993) "Effects of Cytidine Diphosphate Choline on Rats with Memory Deficits." Drug Res. 822-828.
Secades, et al (1995) "CDP-Choline: Pharmalogical and Clinical Review." Methods Find Exp Clin. Pharmacol. 1-54.
Page et al., "Developmental Disorder Associate with Increased Cellular Nucleotidsase Activity," Proc. Natl. Acad. Sci USA, 94(21), 11601-11606 (Oct. 14, 1997).
Coirault R, Levy J, Michel-Ber E, Masbernard A, Desclos De La Fonchais S, Mazingant F.[Uridine-5-triphosphoric acid in therapeutics. 1. Treatment of neurogenic muscular atrophy.] Presse Med. Jun. 18, 1960;68:1127-9. French.
Merlini et al., Effects of Large Doses of Pyrimidine Nucleosides Cytidine and Uridine in Elderly Patients with Neuropsychological Disturbances Caused by Vascular and Cerebral Metabolic Insufficiency, Gazzetta Medica Italiana Archivio Scienze Mediche, 145(6), 379-390 (Jun. 1966); Biological Abtracts, 83, Abstract No. 27367 (1987).
Gallai et al. (I), Effects of Uridine in the Treatment of Diabetic Neuropathy: An Electrophysiological Study, Acta Neurol. Scand., 86(1), 3-7 (1992); Biological Abtracts, 94, Abstract No. 112030 (1992).
Gallai et al. (II), Multi-Infarct Dementia: Modification of the P300 Cognitive Event-Related Potential in Patients Treated with the Association of Cytidine and Uridine, Rivista di Neuropsichiatria e Science Affini, 41(1), 1-9 (1995); BIOSIS, 1996, Abstract Citation No. 466219; only Abstract supplied.
Drago et al., Memory Deficits of Aged Male Rats Can Be Improved by Pyrimidine Nucleosides and N-Acetylglutamine, Clinical Neuropharmacology, 13(4), 290-296 (1990); Biological Abstracts, 90, Abstract No. 91117 (1990).
Manna et al., Effects of Short-Term Administration of Cytidine, Uridine and L-Glutamine Alone or in Combination on the Cerebral Electrical Activity of Patients with Chronic Cerebrovascular Disease, Intl. Journal Clinical Pharmacology Research, 8(3), 199-210 (1988); Biological Abstracts, 86, Abstract No. 51989 (1988).
Kellbaugh et al., Anti-Human Immunodeficiency Virus Type 1 Therapy and Peripheral Neuropathy: Prevention of $2^2$, $3^2$-Dideoxycytidine Toxicity in PC12 Cells, a Neuronal Model, by Uridine and Pyruvate, Molecular Pharmacology, 44(4), 702-706 (Oct. 1, 1993); BIOSIS, 1994, Abstract Citation No. 413648.
Popov et al., Protective Effect of Uridine on D-Galactosamine-Induced Deficiency in Brain Uridine Phosphates Biomedica Biochimica Acta, 43(12), 1399-1404 (1984); Biological Abstracts, 80, Abstract No. 34525, (1985).
Miyazakl et al., Effects of Nucleotides on Learning and Memory in a Morris Water Maze Test in Normal and Basal Forebrain-Lesioned Rats, Life Sciences, 64(1), 45-52 (Nov. 27, 1998).
Entingh et al., Brain Uridine Monophosphate: Reduced Incorporation of Uridine During Avoidance Learning, Brain Research, 70(1), 131-138 (Apr. 12, 1974); only abstract supplied.
Ott et al. Some Effects of RNA Precursors on Development and Maintenance of Long-Term Memory: Hippocampal and Cortical Pro- and Post-Training Application of RNA Precursors, Psychopharmacologia, 28(2), 195-204 (1973).
Ott et al. (II), Influence of 6-aza-uridine on facilitation of relearning by precursors of ribonucleic acid, Psychopharmacologia, 23(3), 272-278 (1972); Chemical Abstracts, 76(25), p. 103, Abstr. No. 149588z, (Jun. 19, 1972).
Gibbons et al., Biochemistry of Cholesterol, Elsevier Biomedical Press, New York, NY, 1982, only pp. 258 and 259 supplied.
Lodish et al., Molecular Cell Biology, W. H. Freeman & Co., New York, NY, 2000, only pp. 68-78 supplied, see especially pp. 75-76.
Kato et al., Determinants of Sex Hormone Levels in Men as Useful Indices in Hormone-Related Disorders, Journal of Clinical Epidemiology, 45(12), 1417-1421 (Dec. 1992).
Vincent, Albert L. et al., The Pathology of the Mongolian Gerbil (Meriones unguiculatus): A Review, Laboratory Animal Science, pp. 645-651, (Oct. 1979).
Ross, B. et al., (1997) Phospholipid Biosynthetic Enzymes in Human Brain. Lipids 32, 351-358.
Cornford et al., Independent blood-brain barrier transport systems for nucleic acid precursors. Biochim. Biophys Acta, 349:211-219, (Jun. 25, 1975).
Dawson. Enzymic conversion of uridine nucleotide to cytidine nucleotide by rat brain. J. Neurochem., 15:31-34, (Jan. 1968).
Becroft DM, et al., Hereditary orotic aciduria: long-term therapy with uridine and a trial of uracil. J Pediatr., 75(5): 885-891, (Oct. 1969).
Roberts CA, et al., Uridine anticonvulsant effects: selective control of nucleoside incorporation in experimental epilepsy. Epilepsia, 15(4): 479-500, (Dec. 1974).
Monticone GF, et al., On the therapeutic use of nucleosides, cytidine and uridine, in some neurological diseases. Minerva Med., 57(101): 4348-4352, (Dec. 19, 1966).
Lopez-Coviella et al., Evidence that 5-cytidinephosphocholine can affect brain phospholipid composition by increasing choline and cytidine plasma levels. J. Neurochemistry, 65: 889-894, (Aug. 1995).
Ginsburg et al., Rodent models of cerebral ischemia. Stroke 20:1627-1642, (Dec. 1989).
D'Orlando et al. "Citicoline (CDP-choline): mechanisms of action and effects in ischemic brain injury." Neurol. Res., vol. 17(4), pp. 281-284. Aug. 1995.
Hull A.M., "Neuroimaging findings in post-traumatic stress disorder." Br. J. Psychiatry. Aug. 2002, vol. 101, pp. 102-110; abstract.
Pawlak R et al. "Tissue plasminogen activator and plasminogen mediate stress-induced decline of neuronal and cognitive functions in the mouse hippocampus." Proc. Natl. Acad. Sci. USA. Dec. 13, 2005, vol. 102, No. 50, pp. 18201-18206; abstract.
Fujio et al. Biosci. Biotechnol. Biochem., vol. 61 (6), pp. 956-959. Jun. 1997.
Osada et al. Br. J. Nutr., vol. 62 (2), pp. 343-348. Sep. 1989.
Cacabelos et al "Therapeutic Effects of CDP-Choline in Alzheimer's Disease Cognition, Brain Mapping, Cerebrovascular hemodynamics, and Immune Factors" Annals of the New York Academy of Sciences, New York Academy of Sciences, New York, NY, US, 1996, p. 399-403, ISSN: 0077-8923 abstract.
Spiers et al "Citicoline Improves Verbal Memory in Aging" Archives of Neuroology, American Medical Association, vol. 43, No. 5, 1996, pp. 441-448.
Styrer Lubert: "Biochemistry", Third Edition, W.H. Freeman and Company / New York; 1988, p. 550.

(56) References Cited

OTHER PUBLICATIONS

Terry R.D. et al.: "Physical basis of cognitive alteration in Alzheimer's disease: synapse loss is the major correlate of cognitive impairment". Ann. Neurol., (1991), 30:572-580.
Berckendridge W.C. et al.: "The lipid composition of adult rat brain synaptosomal plasma membranes", Biochim. Biophys. Acta, (1972), 266:695-707.
Choy P. et al.: "An increase in cytoplasmic CTP accelerates the reaction catalysed by CTP: phosphocholine cytidyltransferase in poliovirus-infected HeLa". The Journal of Biological Chemistry, (1980); 255(3): 1070-1073.
Albright et al "Choline Availability Alters Embroyo Development of the Hippocampus and Septum in the Rat", Developmental Brain Research, 113 13-20(1999).
Jansen et al "Biosynthesis of Phosphatidylcholine from a Phosphocholine Precurser Pool Derived from the Late Endosomal/Lysosomal Degradation of Sphingomyelin" J.Biological Chemisty, 276(22), 18722-18727 (2001).
O'Neil et al The Merck Index, An Encyclopeida of Chemicals, Drugs, and Biologicals, 13$^{th}$ Edition, 2001, Merck & Co. Whitehouse Station, NJ, p. 404.
Testa et al., "Produrg Research: futile or fertile?" Biochemical Pharmacology (2004) vol. 68 pp. 2097-2106.
Silverman, "The Organic Chemistry of Drug Design and Drug Action" Published 1992 by Academic Press, pp. 4-47.
The Merck manual of Diagnosis and Therapy, published 1999 by Merck Research Laboratories, pp. 1382-1383 an d1393-1400.
Khedr et al., "Neural Matruation of Breastfed and Formula-fed Infants" Acta Pediatr (2004) vol. 93 pp. 734-738.
Valenzuela A. et al. "Docosahexaenoic acid (DHA) in fetal development and in infant nutrition". Rev Med Chill Oct. 2001; 129(10); 1203-11, Abstract, found Jun. 29, 2010 in PubMed PMID: 11775350.
Wurtman, "Synapse Formation and Cognitive Brain Development: effect of docosahexaenoic (DHA) and other dietary constituents" Metabolism (2008) vol. 57 suppl 2, S6-10.
Yehuda S. et al., "Modulation of learning, pain thresholds, and thermoregulations in the rat by preparations of free purified alphalinolenic and linolenic acids; determination of the optimal omga 3- to omega-6 ratio". Proc Natl Acad Sci USA A. Nov. 1, 1993;90(21):10345-9.
Spanner S. and Ansell G. B. (1979) Choline kinase and ethanolamine kinase activity in the cytosol of nerve endings from rat forebrain. *Biochem. J.*
Spector A. A. (2001) Plasma free fatty acid and lipoproteins as sources of polyunsaturated fatty acid for the brain. *J. Mol. Neurosci.* 16, 159-165.
Stalenhoef A. F. H., DeGraaf J., Wittekoek M. E., Bredie S. J. H., Demacker P. N. M. and Kastelein J. J. P. (2000) The effect of concentrated n-3 fatty acids versus gemfibrozil on plasma lipoproteins, low density lipoprotein heterogeneity and oxidizability in patients with hypertriglyceridemia. *Atherosclerosis* 153, 129-138.
Suzuki N. N., Koizumi K., Fukushima M., Matsuda A., and Inagaki F. (2004) Structural basis for the specifity, catalysis, and regulation of human uridine-cytidine kinase. *Structure* 12, 751-764.
Svanborg A. and Svennerholm L. (1961) Plasma total lipids, cholesterol, triglycerides, phospholipids and free fatty acids in a healthy Scandinavian population. *Acta Med. Scand.* 169, 43-49.
Teather L. A. and Wurtman R. J. (2005) Dietary CDP-choline supplementation prevents memory impairment caused by impoverished environmental conditions in rats. *Learn. Mem.* 12, 39-43.
Ulus I. H., Wurtman R. J., Mauron C. and Blusztajn J. K. (1989) Choline increases acetylcholine release and protects against the stimulation-induced decrease in phosphatide levels within membranes. *Brain Res.* 484, 217-227.
Wang L., Pooler A. M., Regan M. A. and Wurtman R. J. (2004) Uridine increases neurotransmitter release in aged rats. 34$^{th}$ Society for Neuroscience Abstracts, Oct. 23-27, San Diego, CA. USA.
Wang L., Pooler A. M., Regan M. A. and Wurtman R. J. (2005) Dietary uridine-5'-monophosphate supplementation increases potassium-induced dopamine release and promotes neurite outgrowth in aged rats. *J. Mol. Neurosci.* 27, 137-146.
Araki W. and Wurtman R. J. (1997) Control of membrane phosphatidylcholine biosynthesis by diacylglycerol levels in neuronal cells undergoing neurite outgrowth. Proc. Natl. Acad. Sci. USA 94, 11946-11950.
Babb S. M., Ke Y., Lange N., Kaufman M. J., Renshaw P. F., and Cohen B. M. (2004) Oral choline increases choline metabolites in human brain. Psychiatry Res. 130, 1-9.
Cansev M., Watkins C. J., van der Beek E. M., Wurtman R. J. (2005) Oral Uridine 5' monophosphate (UMP) increases brain CDP-choline levels in gerbils. Brain Res. 1058, 101-108.
Cansev M. and Wurtman R. J. (2005) Exogenous cytidine-5'-diphosphocholine increases brain cytidine-5'-diphosphocholine levels in gerbils. 20th Biennial Meeting of the ISNESN Abstracts, Aug. 21-26, 2005, Innsbruck, Austria, J. Neurochem. 94 (Supp. 2), 105-106.
Cao D., Xue R., Xu J., and Liu Z. (2005) Effects of docosahexaenoic acid on the survival and neurite outgrowth of rat cortical neurons in primary cultures. *J. Nutr. Biochem.* 16, 538-546.
Cohen E. L. and Wurtman R. J. (1976) Brain acetylcholine: control by dietary choline. *Science* 191, 561-562.
Coleman P., Federoff H., and Kurlan R. (2004) A focus on the synapse for neuroprotection in Alzheimer disease and other dementias. *Neurology* 63, 1155-1162.
Cornford E. M., Braun L. D., and Oldendorf W. H. (1978) Carrier mediated blood-brain barrier transport of choline and certain choline analogs. *J. Neurochem.* 30, 299-308.
Fenton WS, Dickerson F, Boronow J, Hibbeln JR, Knable M. (2001) A placebo-controlled trial of omega-3 fatty acid (ethyl eicosapentaenoic acid) supplementation for residual symptoms and cognitive impairment in schizophrenia. Am J Psychiatry. Dec. ;158(12):2071-4.
Ferreira A. and Rapoport M. (2002) The synapsins: beyond the regulation of neurotransmitter release. *Cell. Mol. Life Sci.* 59, 589-595.
Folch J., Lees M., and Sloane-Stanley G. H. (1957) A simple method for the isolation and purification of total lipides from animal tissues. *J. Biol Chem.* 226, 497-509.
Fujita A. and Kurachi Y. (2000) SAP family proteins. *Biochem. Biophys. Res. Commun.* 269, 1-6.
Genchev D. D. and Mandel P. (1974) CTP synthetase activity in neonatal and adult rat brain. *J. Neurochem.* 22, 1027-1030.
Harris W. S. (2005) Omega-3 fatty acids, in Encyclopedia of Dietary Supplements, (Coates P. M., Blackman M. R., Cragg G. M., Levine M., Moss J. and White J. D., eds), pp. 493-504. Marcel Dekker, New York.
Hashimoto M., Hossain S., Shimada T., Sugioka K., Yamasaki H., Fujii Y., Ishibashi Y., Oka J-I., and Shido O. (2002) Docosnahexaenoic acid provides protection from impairment of learning ability in Alzheimer's disease model rats. *J. Neurochem.* 81, 1084-1091.
Kennedy E. M. and Weiss S. B. (1956) The function of cytidine coenzymes in the biosynthesis of phospholipids. *J. Biol. Chem.* 222, 193-214.
Knapp S. and Wurtman R. J. (1999) Enhancement of free fatty acid incorporation into phospholipids by choline plus cytidine. *Brain Res.* 822, 52-59.
Labarca C. and Paigen K. (1980) A simple, rapid and sensitive DNA assay procedure. *Anal. Biochem.* 102, 344-352.
Lee V., Trojanowsky J. Q. and Schlaepfer W. W. (1982) Induction of neurofilament triplet proteins in PC12 cells by nerve growth factor. *Brain Res.* 238, 169-180.
Li J. Y., Boado R. J., and Pardridge W. M. (2001) Cloned blood-brain barrier adenosine transporter is identical to the rat concentrative Na+ nucleoside cotransporter CNT2. *J. Cereb. Blood Flow Metab.* 21, 929-936.
Marszalek J. R., Kitidis C., DiRusso C. C., and Lodish H. F. (2005) Long-chain acyl-Coa synthetase 6 preferentially promotes DHA metabolism. *J. Biol. Chem.* 280, 10817-10826.
Champoux M. et al (2002) "Fatty Acid Formula Supplementation and Neuromotor Development in Rhesys Monkey Neonates" Pediatric Research, vol. 51, No. 3.

(56) References Cited

OTHER PUBLICATIONS

Marszalek J. R. and Lodish H. F. (2005) Docosahexaenoic acid, fatty acid-interacting proteins, and neuronal function: breastmilk and fish are good for you. Annu. Rev. Cell Dev. Biol. 21:633-57.

McCann J. C. and Ames B. N. Is docosahexaenoic acid, an n-3 long-chain polyunsaturated fatty acid, required for development of normal brain function? An overview of evidence from cognitive and behavioral tests in humans and animals. Am J Clin Nutr 2005;82:281-95.

Nitooh R. M., Blusztajn J. K., Pittas A. G., Slack B. E., Growdon J. H., and Wurtman R. J. (1992) Evidence for a membrane defect in Alzheimer disease brain. *Proc. Natl. Acad. Sci. USA* 89, 1671.

Pooler A. M., Guez D. H., Benedictus R., and Wurtman R. J. (2005) Uridine enhances neurite outgrowth in nerve growth factor-differentiated pheochromocytoma cells. pp. 207-214.

Rapoport S. I. (2001) In vivo fatty acid incorporation into brain phospholipids in relation to plasma availability, signal transduction and membrane remodeling. *J. Mol. Neurosci.* 16, 243.

Selkoe D. J. (2002) Alzheimer's disease is a synaptic failure. *Science* 298, 789.

Simopoulos AP, Leaf A, Salem N Jr. (1999) Workshop on the Essentiality of and Recommended Dietary Intakes for Omega-6 and Omega-3 Fatty Acids. Journal of the American College of Nutrition, vol. 18, No. 5, 487-489.

Soderberg M., Edlund C., Kristensson K., and Dallner G. (1991) Fatty acid composition of brain phosholipids in aging and in Alzheimer's disease. *Lipids* 26, 421.

Vyh Yu. (2002) Scientific rationale and benefits of nucleotide supplementation of infant formula. *J. Pediatr. Child Health* 38, 543-549.

Carlezon W.A. et al (2005) "Antidepressant-like Effects of Uridine and Omega-3 Fatty Acids are Potentiated by Combined Treament in Rats" Biol Psychiatry 2005, 57;343-350.

Willatts P et al (1998) "Effect of long-chain polyunsaturated fatty acids in infant formula on problem solving at 10 months of age" The Lancet, vol. 352.

Carlson S. E. et al (1996) "A Randomized Trial of Visual Attention of Preterm Infants Fed Docosahexaenoic Acid Until Two Months" Lipids, vol. 31 No. 1.

Birch E.E. et al (2000) "A randomized controlled trial of early dietary supply of long-chain polyunsaturated fatty acids and mental development in term infants" Developmental Medicine & Child Neurology 42: 174-181.

Solfrizzi V. et al (2005) "Dietary fatty acids intake: possible role in cognitive decline and dementia" Experimental Gerontology 40, 257-270.

Lim Giselle P. et al (2005) "A Diet Enriched with the Omega-3 Fatty Acid Docosahexaenoic Acid Reduces Amyloid Burden in an Aged Alzheimer Mouse Model" The Journal of Neuroscience, Mar. 23, 2005—25(12):3032-3040.

MacLean C. H. et al (2005) "Effects of Omega-3 fatty Acids on Cognitive Funxtion with Aging, Dementia, and Neurological Diseases" AHRQ Publication No. 05-E011-2, Feb. 2005.

Morris M. C. et al (2003) "Consumption of Fish and n-3 Fatty Acids and Risk of Incident Alzheimer Disease" Arch Neurol, vol. 60.

Agut J, Ortiz JA. "Age-related changes in memory and their pharmacologic modulation" Ann N Y Acad Sci. (1991)640:295-7. PMID: 1776755.

Lozano Fernandez R. "Efficacy and safety of oral CDP-choline. Drug surveillance study in 2817 cases". Arzneimittelforschung. (1983)33(7A):1073-80. PMID: 6684470.

Crawford et al. www.thelancet.com vol. 366, Aug. 27, 2005.

Fischer et al. Arachidonate has Protumor—Promoting Action that is Inhibited by Linoleate in Mouse Skin Carcinogenesis, The Journal of Nutrition, Apr. 1996, 126, 4S, Research Library Core, p. 1099S.

Montero et al. Increased glutamate, GABA and glutamine in lateral geniculate nucleus but not in medial geniculate nucleus caused by visual attention to novelty. Brain Research 2001, vol. 916, pp. 152-158.

De La Mora et al., Effects of the vigilance promoting drug modafinil on the synthesis of GABA and glutamate in slices of rat hypothalamus. Neuroscience Letters, 1999, vol. 259, pp. 181-185.

Sepkuty et al., A Neuronal Gluamate Transporter Contributes to Neurotransmitter GABA Synthesis and Epilepsy. The Journal of Neuroscience, Aug. 2002, vol. 22, No. 15, pp. 6372-6379.

Beers et al. (eds.), a portion of "Nutritional Disorders," Chapter 1 in The Merck Manual of Diagnosis and Therapy. 17th Edition, Merck & Co., Inc., Rahway, NJ, Jan. 1999, only title and text pp. 1 & 12-21 supplied.

Cohen et al., JAMA 274:902, 1995.

Millington & Wurtman, J. Neurochem 38:1748-1752, 1982.

Nelson & Cox, Lehninger Principles of Biochemistry, Fourth Ed., W.H. Freeman & Co., New York, NY, 2005, only pp. 398-400, 410-411 and 426-427 supplied.

Rüthrich et al., "Increase of Guanosine Incorporation into RNA of . . . Application of Uridine Monophosphate During a Learning Experiments," Brain Research 69(1), 49-55 (Mar. 29, 1974).

Schneider-Helmert and Spinweber, Psychopharmacology (Berl). 1986, 89(1):1-7.

Venes et al. (eds.), Taber's Cyclopedic Medical Dictionary, 19th Ed., F.A. Davis Co., Philadelphia, PA, 2001, see pp. 594 ("differentiation"), 1225 ("Lewy bodies") and 1656 ("Pick's disease").

Werler et al., American Journal of Public Health, vol. 89, Issue 11 1637-1640, 1999.

Wurtman; Sourches of Choline and Lecithin in the Diet, Nutrition & The Brain, vol. 5, A. Barbeau, J.H. Growdon & R.J. Wurtman, eds, Raven Press, New York, 1979, pp. 73-81.

Yates et al., Dietary Reference Intakes: The new basis for recommendations for calcium and related nutrients, B vitamins and choline. J. Am Dietetics Assn, Jun. 1998, vol. 98 No. 6:699-706.

Mosharrof A. H. et al., "Effects of Meclofenoxate and Citicholine on Learning and Memory in Aged Rats" ACTA Physiologica et Pharmacologica Bulgarica, vol. 13, No. 4 Sofia, 17-24, 1987.

de la Morena, E., "Efficacy of CDP-choline in the Treatment of Senile Alterations in Memory," Annals NY Acad, Sci,, 640, 233-236, 1991.

Patel, S. V., "Pharmacotherapy of Cognitive Impairment in Alzheimer's Disease: A Review" J. Geriatric Psychiatry and Neurology, 8, 81-95, 1995.

Richardson, I. U. et al., "Stimulation of CDT-Choline Synthesis by Uridin or Cytidine in PC12 Rat Pheochromocytoma Cells," Brain Research, 971, 161-167, 2003.

Teather L. A. et al., "Dietary Cytidine (5')-diphosphocholine Supplementation Protects against Development of Memory Deficits in Aging Rats," Progress in Neuro-Psychopharmacology & Biological Psychiatry 27, 711-717, 2003.

Conant R. et al. "Therapeutic Applications of Citicoline for Stroke and Cognitive Dysfunction in the Elderly: A Review of the Literature" Alternative Medicine Review, vol. 9, No. 1, 17-31, 2004.

M. Fioravanti et al., "Cytidinediphosphocholine (CDP-choline) for Cognitive and Behavioural Disturbances Associated with Chronic cCerebral Disorders in the Elderly," Cochrane Database of Systematic Reviews, Issue 2, Art No. CD000269, pp. 1-28, 2005.

International Search Report and Written Opinion of corresponding PCT application No. PCT/US08/82265 dated Jan. 6, 2009.

Cansev et al., "Uridine and cytidine in the brain: Their transport and utilization," Brain Research Reviews, Elsevier, NL, vol. 52, No. 2, 2006, pp. 389-397.

Cecil, Kim M. et al., "Magnetic Resonance Spectroscopy of the Pediatric Brain," Topics in Magnetic Resonance Imaging, vol. 12, No. 6, 2001, pp. 435-452.

Extended Search Report of corresponding European application No. 08844229 dated Dec. 23, 2011.

* cited by examiner

URIDINE DIETARY SUPPLEMENTATION COMPLIANCE METHODS AND USE THEREOF

CROSS REFERENCE TO RELATED APPLICATIONS

This application claims priority from U.S. Provisional Patent Application No. 60/996,146, filed Nov. 2, 2007, which is incorporated herein by reference in its entirety.

FIELD OF INVENTION

This invention is directed to determining the compliance of a subject receiving dietary supplementation with uridine or a uridine source. Specifically, the invention is directed to the use of magnetic resonance spectroscopy for measuring an increase in brain compounds resulting from dietary supplementation with uridine or a uridine source.

BACKGROUND OF THE INVENTION

The administration of uridine or uridine precursors to humans can be as beneficial as the administration of cytidine or cytidine precursors. However, the potential benefit of uridine or uridine source dietary supplementation is overwhelmingly greater than the benefit of cytidine administration. This is due to the fact that cytidine, as opposed to uridine, either cannot cross or is much less efficient than uridine in crossing the blood-brain barrier.

Magnetic resonance spectroscopy (MRS) allows for analysis of brain chemistry in vivo. A strong correlation was reported between IQ and brain pH, as determined from $^{31}$P-MRS in normal subjects, although a study of the temporal lobe in epileptic patients failed to replicate this finding. Proton MRS ($^{1}$H-MRS) detects signals from neurometabolites including N-acetylaspartate (NAA) and creatine (Cre)- and choline (Cho)-containing compounds, showing impaired cognition and poor functional outcome.

It has been shown that dietary supplementation increases membrane synthesis, stimulates release of cholinergic compounds and improves cognitive abilities in several pathologies such as Alzheimer's Disease and Parkinson's Disease.

Therefore, there is a need for monitoring and validating the compliance of subjects in adherence to supplementation regimens as well as for the validation of treatment efficacy.

SUMMARY OF THE INVENTION

In one embodiment, the invention provides a method of evaluating a subject's compliance with a uridine dietary supplementation regimen, said method comprising: determining said subject's brain cytidine-containing compound level; and using said brain cytidine-containing compound level to evaluate the subject's compliance with the uridine dietary supplementation regimen.

In another embodiment, the invention provides a method of measuring an increase in brain components in a subject, resulting from a dietary supplementation of uridine or a uridine source comprising the steps of: using magnetic resonance imaging (MRI), localizing the brain region where the increase in brain components occurs; isolating a volume of interest (VOI); defining the voxel size of the VOI; and using localized proton MRS, quantifying the levels of the brain component.

Other features and advantages of the present invention will become apparent from the following detailed description and examples. It should be understood, however, that the detailed description and the specific examples while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

This invention relates in one embodiment to a method of determining the compliance of a subject receiving dietary supplementation with uridine or a uridine source. In another embodiment, the invention provides a method for the use of MRS for measuring an increase in brain compounds resulting from dietary supplementation with uridine or a uridine source.

In one embodiment, the compound to be measured by MRS in brains of people given a uridine-containing compound is endogenous cytidine 5'-diphosphocholine (CDP-choline), the immediate precursor of phosphatidyl choline (PC). Since the choline in brain CDP-choline is readily identifiable using hydrogen spectra, as are the two phosphates in each molecule by using phosphorus spectra, there are two ways of identifying and measuring this compound in a person's brain—or both $^{1}$H and $^{31}$P spectra could be analyzed in a single human subject, providing unusually strong confirmation of what's being measured.

In another embodiment, a single oral dose of uridine 5'-monophosphate (UMP) results first in a rise of plasma uridine and cytidine, then brain uridine and cytidine, followed in another embodiment, by brain uridine 5'-triphosphate (UTP) and cytidine 5'-triphosphate (CTP) (which is rate-limiting in phosphatide synthesis), then brain CDP-choline. The increases in CTP and CDP-choline are substantial but short-lived (i.e., less than an hour). In one embodiment, the rise associated with uridine or a uridine source dietary supplementation after 4 days to a week, is sufficient to produce the elevations in brain phosphatides that are monitored in another embodiment by the methods described herein. The duration and dose relationships of the dietary supplementation regimen will depend in one embodiment on metabolic rates, or in another embodiment on underlying pathology, age, other dietary supplementations and the like.

Accordingly, one embodiment, provided herein, is a method of evaluating a subject's compliance with a uridine dietary supplementation regimen, said method comprising: determining said subject's brain cytidine-containing compound level; and using said brain cytidine-containing compound level to evaluate the subject's compliance with the uridine dietary supplementation regimen. In one embodiment, the step of determining the subject's brain cytidine-containing compound level is via in vivo magnetic resonance spectroscopy (MRS).

In one embodiment, Magnetic Resonance Spectroscopy (MRS) allows for analysis of brain chemistry in vivo. Proton MRS (1H-MRS) detects signals from neurometabolites comprising N-acetylaspartate (NAA), creatine (Cre)-, choline (Cho)-containing compounds or their combination in certain embodiments. The Cho-peak reflects in one embodiment the sum of all visible Cho-moieties, such as in one embodiment glycerophosphocholine and phosphocholine. In one embodiment, the brain compound measured in the methods described herein is choline, or CDP-choline in other embodiments.

In another embodiment, $^{1}$H-MRS measurements of neurometabolic concentrations are associated with intellectual and/or cognitive functioning in the normal human brain. In one embodiment, the brain cytidine-containing compound increased by the dietary supplementation of uridine or a uridine source, is selected from the group of CDP-choline cytidine, cytidine 5'-monophosphate (CMP), cytidine 5'-diphosphate (CDP), cytidine 5'-triphosphate (CTP), deoxycytidine 5'-monophosphate (dCMP), deoxycytidine 5'-diphosphate (dCDP), deoxycytidine 5'-triphosphate (dCTP) and any combination thereof.

In one embodiment the conversion of free choline to membrane phosphatidylcholine (PC) involves its phosphorylation to phosphocholine; the reaction of phosphocholine with cytidine 5'-triphosphate (CTP) to yield cytidine 5'-diphosphocholine (CDP-choline) ; and the transfer of that compound's phosphocholine moiety to the free hydroxyl group of diacylglycerol (DAG). The rates of all three reactions may be influenced in another embodiment by substrate availability; CTP levels may limit the formation of endogenous CDP-choline; and DAG levels increased when PC12 cells are differentiated by treatment with nerve growth factor (NGF), and may control the rate at which these cells convert CDP-choline to PC. In another embodiment, the rate-limiting step in PC synthesis is the formation of CDP-choline from CTP and phosphocholine. Brain CTP levels are lower in one embodiment, than those needed to saturate the enzyme (CTP: phosphocholine cytidylyltransferase) that catalyses this reaction, thus giving cytidine, which increases brain CTP, accelerates PC synthesis in both PC12 cells. In another embodiment, incubation of PC12 cells with uridine, which is converted to UTP and CTP enhances the formation of CDP-choline, the immediate precursor of PC.

In one embodiment, cholinergic neurons both acetylate and phosphorylate choline, to form acetylcholine and phosphocholine (and, in another embodiment, phosphatidylcholine); the acetylation pathway is favored over phosphorylation when the neurons are depolarized. In another embodiment addition of choline to the perfusion medium both increases acetylcholine synthesis and release, and in another embodiment enhances membrane phospholipid synthesis.

In one embodiment, uridine, the primary circulating pyrimidine in humans is readily converted in the brain to UTP and then CTP and affects acetylcholine synthesis and release. In another embodiment, the uridine dietary supplementation regimen is given to a subject for the treatment of a neurodegenerative disorder, or for the treatment of a memory impairment disorder in another embodiment, or for the treatment of a learning disorder such as, for instance, Attention-Deficit Disorder (ADD) and Attention-Deficit Hyperactivity Disorder (ADHD)) in another embodiment, or their combination in another embodiment, each being a discrete embodiment of the methods described herein. In one embodiment, the uridine source for which the brain compounds increase, resulting from the dietary supplementation regimen which compliance is monitored using the methods described herein, is selected from the group of uridine, uridine 5'-monophosphate (UMP), uridine 5'-diphosphate (UDP), uridine 5'-triphosphate (UTP), uridine 5'-diphosphate glucose (UDP-glucose), their nutritional or pharmaceutical acceptable salts, and any combination thereof.

In another embodiment, the neurodegenerative disorder for which the brain compounds increase, resulting from the dietary supplementation regimen which compliance is monitored using the methods described herein, is selected from the group of Parkinson's Disease (PD), Alzheimer's Disease (AD), Huntington's Disease (HD), Amyotrophic Lateral Sclerosis (ALS), Atriplet Repeat Disease (ARD), Friedreich's Ataxia, stroke, multi-infarct, dementia, multiple sclerosis, chronic fatigue, schizophrenia, cerebral palsy, traumatic brain injury and any combination thereof in other discrete embodiments of the methods described herein.

In one embodiment, the memory impairment disorder for which the brain compounds increase, resulting from the dietary supplementation regimen which compliance is monitored using the methods described herein, is selected from the group of Parkinson's-related dementia, Alzheimer's disease related dementia, or stroke. In one embodiment, $^1$H-MRS provides measures of neuronal injury and/or viability in overt disease, such as traumatic brain injury.

In one embodiment, the dietary supplementation comprises uridine or a uridine source, as well as a dietary supplementation of an omega-3 fatty acid (e.g. Docosahexaenoic acid (DHA), Eicosapentaenoic acid (EPA), or both), a choline source, and their combination in other discrete embodiments. In one embodiment, the choline source is selected from the group of choline, acetyl choline, phosphatidyl choline, their nutritional or pharmaceutical acceptable salts, and any combination thereof in other discrete embodiment of the supplemental components of the dietary regimen given in the methods described herein.

In one embodiment, the step of determining the subject's brain compound level comprises the step of using an MRI, localizing the brain region where increased brain compounds are detected prior to MRS; isolating a volume of interest (VOI); defining the voxel size of the VOI; and using a localized proton MRS, and quantifying the levels of brain compounds inside the VOI.

In another embodiment, the methods and compositions described hereinabove, are used for the methods described herein. In another embodiment, provided herein is a method of measuring an increase in a brain components in a subject, resulting from dietary supplementation of uridine or a uridine source comprising the steps of: using magnetic resonance imaging (MRI), localizing the brain region where the increase in brain components occurs; isolating a volume of interest (VOI); defining the voxel size of the VOI; and using localized proton MRS quantifying the levels of the brain component. In one embodiment, the magnetic resonance is of $^1$H, $^{31}$P, $^{13}$C and any combination thereof in another embodiment.

In MRS and MRSI, the dwell time for spectroscopic encoding depends on the nucleus. In proton spectroscopy the spectral range is rather narrow (9 ppm=380 Hz/Tesla) and the necessary dwell time to encode the entire spectral range is on the order of 1.75 ms at 1 Tesla and 0.88 ms at 3 Tesla, which are commonly used field strengths. This is sufficient time between spectral encoding points to interleave magnetic field gradient pulses. Sparse sampling can be implemented in one embodiment, such that the spectral dwell time for linear time domain sampling is increased at the expense of spectral aliasing. A key element of this approach is to select the spectral dwell time such that minimal loss of spectral information is incurred in the aliased spectrum.

The term "about" as used herein, means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

Having described preferred embodiments of the invention, it is to be understood that the invention is not limited to the precise embodiments, and that various changes and modifications may be effected therein by those skilled in the art without departing from the scope or spirit of the invention as defined in the appended claims.

EXAMPLES

Example 1

Magnetic Resonance Spectroscopy

Spectroscopy

MRI and $^1$H-MRS are performed on a 3T scanner. Anatomical MR images are obtained in the coronal plane using a 3D magnetization-prepared rapid gradient echo (MPRAGE) sequence. The sequence is acquired with a field of view of 16 cm, 32 slices with a 3-mm slice thickness, 256×256 matrix size 600-msec inversion time, repetition time (TR) of 8 msec, echo time (TE) of 3 msec, a bandwidth of 32 kHz, and 1 excitation. These images are used to select graphically the left and right hippocampus for solvent suppressed $^1$H-MRS. Single-voxel $^1$H-MRS of the hippocampus is performed using point-resolved spectroscopy (PRESS). The $^1$H spectra ($2 \times 2 \times 3$ cm$^3$) are acquired with a repetition time of 2 sec, time to echo of 35 msec, spectral width of 5,000 Hz, 2,048 time points, and 128 averages (4.3 min) and an eight-step phase cycling scheme. Crusher gradients of 32 mT/m amplitude (80% of the full-scale system gradient amplitude) and a duration of 4 msec (maximum crusher width) are equally spaced around the 180° pulses with 10-msec spacing. Spatial saturation pulses are applied at the edge of the PRESS voxel to minimize contamination of signal from outside the prescribed voxel. Linear shims is used to correct inhomogeneity across the investigated voxel. Spectral analysis is performed using LC-Model, embedded in the Spectroscopy Analysis by GE package (SAGE) (GE Medical Systems, Milwaukee, Wis.). The output of LC-Model gives both the ratios (expressed as relative concentration taking into account the number of protons in each compound) of the uridine source and the resulting cytidine level in the brain and their standard deviations. Peak assignments for the different metabolites are those routinely used.

Data Analysis

Analysis is performed on the main metabolites detected by MRS, that is, CDP choline, cytidine, cytidine 5'-monophosphate (CMP), cytidine 5'-diphosphate (CDP), cytidine 5'-triphosphate (CTP), deoxycytidine 5'-monophosphate (dCMP), deoxycytidine 5'-diphosphate (dCDP), deoxycytidine 5'-triphosphate (dCTP), all expressed as a ratio of the administered uridine (Ur). When modeling the overall correlation between the administered uridine or uridine source and metabolite ratios, the measurements of metabolite ratios from the hippocampus on both sides of the brain of each subject analyzed by using repeated measures, with a compound symmetry covariance structure, to account for the within subject correlation.

Results

Results show a direct correlation between the increase in metabolite ratio as a function of administered uridine or uridine source.

Example 2

1H MRS for Detecting Increase in Cytidine Levels

MRS Methods

All MRI scans and localized in vivo $^1$H MRS procedures are performed on a system equipped with shielded gradients (GE 1.5T Signa; General Electric Medical Systems; Milwaukee, Wis.) from 9 PM to midnight. Spectroscopy is performed following a routine brain MRI analysis, and the $T_2$-weighted images are used for localization of an area of interest. Image-guided stimulated echo acquisition mode spectra is obtained from the parietal white matter (PWM) and the occipital gray matter (OGM) regions (with proton brain examination) with the following acquisition parameters: echo time, 30 ms; repetition time, 3.0 s; number of averages, 36; spectral width, 2,500 Hz; spectral size, 2,048 points (General Electric Medical System). The voxels used in this study have volumes of 7 to 9 mL, and a three-pulse chemical shift selective sequence is used for the suppression of the $H_2O$ signal. Placement of the localization voxel in the same region is done by a professional for all subjects, thereby increasing the consistency of region selection.

The major metabolites detectable in $^1$H MRS are CDP choline, cytidine, cytidine 5'-monophosphate (CMP), cytidine 5'-diphosphate (CDP), cytidine 5'-triphosphate (CTP), deoxycytidine 5'-monophosphate (dCMP), deoxycytidine 5'-diphosphate (dCDP), deoxycytidine 5'-triphosphate (dCTP). Peaks are identified with known chemical shifts. The raw spectroscopic data is transferred to a computer workstation and processed by special software (SA/GE; General Electric Medical Systems). The areas under the peaks is measured by Lorenzian line-shape fitting. The absolute concentrations of CDP choline, cytidine, cytidine 5'-monophosphate (CMP), cytidine 5'-diphosphate (CDP), cytidine 5'-triphosphate (CTP), deoxycytidine 5'-monophosphate (dCMP), deoxycytidine 5'-diphosphate (dCDP), deoxycytidine 5'-triphosphate (dCTP) is calculated from the processed spectrum using the brain water as an internal reference. All concentrations are expressed as millimoles per weight of uridine taken. The reference brain water signals used is fixed in the PWM and in the OGM, as calculated.

Results show a direct correlation between the increase in metabolite ratio as a function of administered uridine or uridine source.

Example 3

Localized $^{13}$C MRS Measurement of In Vivo $^{13}$C Cytidine in Brain

All in vivo MRS studies are performed in a horizontal 9.4-T/31-cm magnet (Magnex Scientific, UK) with an 11-cm-diameter gradient coil capable of switching to 300 mT/m in 500 µs, interfaced with an INOVA console (Varian Inc., Calif., USA). A quadrature $^1$H radiofrequency (RF) 14-mm-diameter coil and a linear polarized, three-turn 11-mm-diameter $^{13}$C RF coil are used as the transceiver. A sphere containing 99% $^{13}$C-enriched glucose (Glu) is located at the center of the $^{13}$C coil as an external reference, and the coil is placed on the subject's head. Fast Automatic Shimming Technique by Mapping Along Projections (FASTMAP) shimming with echo-planar imaging (EPI) readout is applied to adjust $B_0$ field homogeneity in a initially nominal ~440 µL volume of interest (VOI). The Single-shot Inversion Recovery based Non-Echo (SIRENE) sequence is applied for 3D localization with optimized outer volume suppression to ensure elimination of signals from noncerebral tissue, and bilevel WALTZ-16 RF pulses are applied at the water frequency for generation of a nuclear Overhauser effect (NOE) and for decoupling during acquisition.

Twelve 64-scan localized $^{13}$C MR spectra (repetition time (TR)=1 s) acquired and are summed, apodized by 20-Hz exponential line-broadening, zero-filled, and Fourier transformed. The brain cytidine C1 signal intensity ( ) is fitted using built-in spectrometer software (Varian Inc.) with a fixed linewidth obtained from the spectrum obtained by summing all acquisitions during the entire measurement is quantified using the external reference method, based on the measurement of the signal from a phantom containing 400 mM of natural abundance cytidine ( ) under identical conditions as for the in vivo measurements, including temperature. In vivo $^{13}$C brain cytidine content ($[^{13}C\text{-}Cyt]_{invivo}$) is calculated. The in vivo signal is corrected with a small correction factor (<15%), which includes measured differential coil loading determined from the obtained labeled Glu signals in reference studies ( ) and in vivo experiments ( ), and NOE/$T_1$ effects are assessed from the fully relaxed cytidine signal obtained in previous preceding tests.

Results show a direct correlation between the increase in metabolite ratio as a function of administered uridine or uridine source.

Having described preferred embodiments of the invention, it is to be understood that the invention is not limited to the precise embodiments and examples and that various changes and modifications may be effected therein by those skilled in the art without departing from the scope or spirit of the invention as defined in the appended claims.

What is claimed is:

1. A method of evaluating a subject's compliance with a uridine dietary supplementation regimen comprising:
    administering a uridine dietary supplement to a subject according to a regimen;
    determining said subject's brain cytidine-containing compound level via in vivo magnetic resonance spectroscopy (MRS) by selecting a brain region of interest where increased cytidine-containing compounds occur optionally using MRI prior to MRS; isolating a volume of interest (VOI) within the brain region of interest; defining the voxel size of the VOI; and using localized proton MRS, quantifying the levels of cytidine-containing compounds inside the VOI; and
    using said brain cytidine-containing compound level to evaluate the subject's compliance with the uridine dietary supplementation regimen, wherein the magnetic resonance spectroscopy is of $^1$H, $^{31}$P, $^{13}$C or a combination thereof.

2. The method of claim 1, wherein the brain cytidine-containing compound is selected from the group of CDP choline, cytidine 5'-diphosphocholine, cytidine, cytidine 5'-monophosphate (CMP), cytidine 5'-diphosphate (CDP), cytidine 5'-triphosphate (CTP), deoxycytidine 5'-monophosphate (dCMP), deoxycytidine 5'-diphosphate (dCDP), deoxy-cytidine 5'-triphosphate (dCTP) and any combination thereof.

3. The method of claim 1, wherein the uridine dietary supplementation regimen comprises a uridine source.

4. The method of claim 3, wherein the uridine source is selected from the group of uridine, uridine 5'-monophosphate, uridine 5'-diphosphate, uridine-5'-triphosphate, uridine-5'-diphosphate glucose, their nutritional or pharmaceutical acceptable salts and any combination thereof.

5. The method of claim 1, wherein the uridine dietary supplementation regimen further comprises a dietary supplementation of an omega-3 fatty acid.

6. The method of claim 5, wherein the omega-3 fatty acid is selected from the group of Docosahexaenoic acid (DHA), Eicosapentaenoic acid (EPA) or both.

7. The method of claim 1, wherein the uridine dietary supplementation regimen further comprises a choline source.

8. The method of claim 7, wherein the choline source is selected from the group of choline, acetyl choline, phosphatidyl choline, their nutritional or pharmaceutical acceptable salts, and any combination thereof.

9. The method of claim 1, wherein the brain region is selected from the group of the left occipitoparietal white matter, the frontal cortex, basal ganglia, and any combination thereof.

10. A method of measuring an increase in a brain components in a subject, resulting from dietary supplementation of uridine or a uridine source comprising the steps of: using magnetic resonance imaging (MRI), localizing the brain region where the increase in brain components occurs; isolating a volume of interest (VOI); defining the voxel size of the VOI; and using localized proton MRS quantifying the levels of the brain component.

11. The method of claim 10, wherein the uridine source is selected from the group of uridine, uridine 5'- monophosphate, uridine 5'-diphosphate, uridine 5'-triphosphate, uridine 5'-diphosphate glucose, their nutritional or pharmaceutical acceptable salts and any combination thereof.

12. The method of claim 10, wherein the brain compound is selected from the group of cytidine, a cytidine-containing compound, a choline-containing compound, and any combination thereof.

13. The method of claim 12, wherein the brain cytidine-containing compound is selected from the group of CDP choline, cytidine 5'-diphosphocholine, cytidine, cytidine 5'-monophosphate (CMP), cytidine 5'-diphosphate (CDP), cytidine 5'-triphosphate (CTP), deoxycytidine 5'-monophosphate (dCMP), deoxycytidine 5'-diphosphate (dCDP), deoxy-cytidine 5'-triphosphate (dCTP) and any combination thereof.

14. The method of claim 12, wherein the magnetic resonance is of $^1$H, $^{31}$P, $^{13}$C and any combination thereof.

* * * * *